United States Patent [19]

Baum et al.

[11] Patent Number: 4,618,734

[45] Date of Patent: Oct. 21, 1986

[54] METHOD OF MAKING AND POLYMERIZING PERFLUOROALKYLENE ACETYLENE COMPOUNDS

[75] Inventors: Kurt Baum, Pasadena; Ronald O. Hunadi, Los Angeles; Clifford D. Bedford, Mountain View, all of Calif.

[73] Assignee: Fluorochem Inc., Asuza, Calif.

[21] Appl. No.: 522,605

[22] Filed: Aug. 12, 1983

Related U.S. Application Data

[60] Continuation-in-part of Ser. No. 412,929, Aug. 30, 1982, abandoned, which is a division of Ser. No. 219,938, Dec. 24, 1980, Pat. No. 4,347,376.

[51] Int. Cl.$^4$ ............................................. C07C 21/22
[52] U.S. Cl. .................................. 570/136; 570/140; 570/155; 570/175; 570/126
[58] Field of Search ......................................... 570/136

[56] References Cited

U.S. PATENT DOCUMENTS 4,347,376 8/1982 Baum et al. .................... 556/466

*Primary Examiner*—Natalie Trousof
*Assistant Examiner*—Joseph A. Boska
*Attorney, Agent, or Firm*—John H. Crowe

[57] ABSTRACT

A perfluoroalkylene $\alpha,\omega$-diacetylene compound having a fluorocarbon chain of from 5 to about 20 carbon atoms between two acetylene end groups, and a method of forming same by first reacting perfluoroalkylene diiodide having the formula $I(CF_2)_nI$, wherein n is a whole number from 5 to about 20, inclusive with bis(trimethylsilyl)acetylene, and converting the reaction product to the diacetylene with KF. The diacetylene has the general formula $HC\equiv C(CF_2)_nC\equiv CH$, wherein n is as set forth above, and it can be polymerized to produce a clear, hard, cross-linked resin suitable for use as a coating on bearings and in the manufacture of aircraft windshields. Monofunctional counterparts of the $HC\equiv C(CF_2)_nC\equiv CH$ compounds can be formed by substituting perfluoroalkyl primary iodides for the diiodides in the above-described reaction. The resulting compounds (fluorinated monofunctional acetylenes) can be trimerized to yield liquids suitable as lubricating oils, hydraulic fluids, etc.

2 Claims, No Drawings

METHOD OF MAKING AND POLYMERIZING PERFLUOROALKYLENE ACETYLENE COMPOUNDS

The Government has rights in this invention pursuant to Contract N00014-78-C-0520 awarded by the Department of the Navy.

CROSS-REFERENCE TO RELATED APPLICATIONS

This application is a continuation-in-part of our copending U.S. application Ser. No. 412,929, filed Aug. 30, 1982, abandoned Feb. 9, 1984, which is a division of U.S. application Ser. No. 219,938, filed Dec. 24, 1980, now U.S. Pat. No. 4,347,376.

BACKGROUND OF THE INVENTION

This invention relates generally to methods of synthesizing perfluoroalkylene compounds and of polymerizing the compounds into formulations having useful commercial properties. More particularly, the invention relates to methods of making novel perfluoroalkylene $\alpha,\omega$-diacetylene compounds and perfluoroalkyl primary acetylenes, and of trimerizing the resulting monomers to form a variety of novel fluorocarbon compositions of unique properties suitable for use in a variety of applications.

Certain flurocarbon resins have, for some time, been employed as heat-resistant coatings on metal surfaces. Such resins are more commonly referred to as Teflon resins. Teflon being a trademark of E. I. duPont for those materials, and they are used to coat a variety of consumer products. Examples of consumer products so coated are frying pans, razor blades, saws, drill bits and hammers. More dramatically, such a coating has been used by NASA on a lunar orbiting vehicle as a shield against the friction of re-entry into the earth's atmosphere. Teflon fluorocarbon coatings have thus found widespread applicability for use in both the consumer product field and the more exotic Space Age hardware field.

While Teflon has, as indicated, found applications as heat-resistant coatings on metal surfaces, it has certain drawbacks which limit its usefulness there and elsewhere. For example, Teflon is formed by linear polymerization, as a result of which it cold-flows under conditions of elevated pressure and/or temperature. This limits its life in certain applications such as, for example, the coating of bearings. Furthermore, Teflon is opaque, making it unsuitable for use where transparent plastic is required.

SUMMARY OF THE INVENTION

We have now, by this invention, provided new methods of synthesizing perfluoroalkylene compounds, some heretofore unknown, and of polymerizing said compounds to form commercially useful products having a variety of applications. Certain of these compounds are perfluoroalkylene diacetylenes of liquid form which can be applied to metal surfaces and polymerized thereon to form tenacious coatings of cross-linked character. The polymerization of these diacetylene compounds, moreover, yields a solid, transparent, cross-linked structure which will not cold-flow at elevated temperatures and pressures and is therefore useful for the coating of bearings, as well as having applicability for aircraft windshield manufacturing, and other, purposes. In line with the foregoing, we found the polymerized material to have thermal stability (DSC) 450° C.

Another class of compounds formed by a method within the scope of this invention comprises certain monofunctional acetylenes which can be trimerized into liquid products useful as lubricating oils, hydraulic fluids and the like.

Chief among the above-mentioned compounds produced by methods in accordance with this invention are perfluoroalkylene $\alpha,\omega$-diacetylenes having a fluorocarbon chain of from about five to about twenty carbon atoms between two acetylene end groups. Our preferred method of making these diacetylenes involves the free-radical-catalyzed addition of a perfluoroalkylene diiodide having the formula $I(CF_2)_nI$, wherein n is a whole number from 5 to about 20, inclusive, to trimethylsilylacetylene, followed by dehydrohalogenation with 1,8-diazabicyclo[5.4.0]undec-7-ene (more commonly known as DBU) under dry conditions to form a substituted trimethylsilylacetylene. The silyl group of the trimethylsilylacetylene is preferably removed with either excess DBU or KF. The general reaction scheme for this method is given below as Reaction Scheme I.

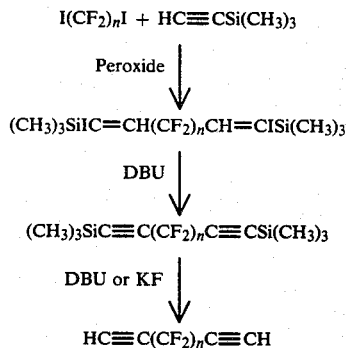

Monofunctional acetylene counterparts of the diacetylene products of Reaction Scheme I can be formed by substituting perfluoroalkyl primary iodides for the above-identified diiodides.

The diacetylene compounds formed by Reaction Scheme I are novel insofar as we are aware, and they can be polymerized under heat to form transparent, cross-linked solids which, because of their cross-linked nature, do not, as previously indicated, cold-flow. They thus constitute a new class of resins suitable for use in areas where known fluorocarbon plastics, such as, for example, Teflon plastic, are unsuitable. Two such use areas (bearing coatings and aircraft windshields) have meen mentioned previously herein.

The monoacetylene compounds referred to above can be trimerized to form monocyclic, rather than cross-linked, compositions which are liquids suitable for use as lubricating oils, waxes, hydraulic fluids, etc. If mixtures of diacetylene and monoacetylene compounds are polymerized in proper proportions, rubbery products will result. With proper adjustment of the $CF_2$ chain lengths of diacetylenes prepared as taught herein, liquid mixtures can be prepared and applied to metal surfaces for in situ polymerization to form coatings thereon which do not have the cold-flow disadvantage of Teflon. Although, as indicated, the above-mentioned diacetylenes are novel, certain fluorinated monoacetylenes have been reported, although neither our novel method of preparing same nor of trimerizing them has, to our knowledge, been heretofore proposed.

In addition to the Reaction Scheme I method identified above, we have come up with an alternative method of preparing the novel diacetylene compounds of this invention. In this alternative method, fluorocarbon diiodides such as those employed in Reaction Scheme I are reacted with bis(trimethylsilyl)acetylene in the presence of quaternary ammonium salts or dimethylformamide. This reaction gives substituted trimethylsilylacetylenes directly, and these are converted to the free acetylenes with KF. The general reaction scheme for this method is set forth below as Reaction Scheme II.

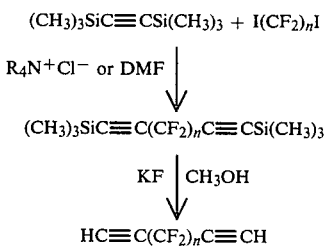

This method gives considerably lower yields than that of Reaction Scheme 1. Similarly to the latter, it can be made to yield monofunctional acetylenes by the substitution of perfluoroalkyl primary iodides for the above-noted diiodies.

DESCRIPTION OF THE PREFERRED EMBODIMENTS

To more fully illustrate this invention, the following examples are presented. It is to be understood, however, that these examples are offered merely as a means of illustration and are not intended to limit the scope of the invention to the particular combinations of materials, conditions, proportions, etc., set forth therein.

EXAMPLE I

Preparation of
1,10-diiodo-1,10-bis(trimethylsilyl)-
3,3,4,4,5,5,6,6,7,7,8,8-dodecafluorodeca-1,9-diene,
$(CH_3)_3SiIC\!=\!CH\!-\!(CF_2)_6CH\!=\!CISi(CH_3)_3$ This example illustrates the first step (addition reaction) of Reaction Scheme I, in which the perfluoroalkylene diiodide employed was 1,6-diiodoperfluorohexane.

A mixture of 3.3 g (6.0 mmol) of 1,6-diiodoperfluorohexane, 1.5 g of trimethylsilylacetylene and 0.5 ml of di-t-butyl peroxide was heated in a sealed glass tube under nitrogen for 85 hrs at 120° C. The product was dissolved in 50 ml of methylene chloride dried over magnesium sulfate and stripped of solvent under vacuum to give 4.2 g (92%) of the title compound as a mixture of E/E, Z/Z and E/Z isomers, analytically pure without further treatment: proton NMR CDCl$_3$δ7.23(t, $J_{HF}$=15 Hz, =CH—, E isomers), δ6.60 (T, $J_{HF}$=13 Hz, =CH—, Z isomers) 0.35 (t, CH$_3$Si, E isomers) and 0.25 ppm (s, CH$_3$Si, Z isomers); fluorine NMR (CDCl$_3$) φ 108.4 (m, =CH—CF$_2$—,E isomers), 111.6 (m, =CH—CF$_2$—,E isomers), 111.6 (m, =CH—CF$_2$—, Z isomers), 123.2 (m,CF$_2$ internal) and 124.4 ppm (m, =CH—CF$_2$CF$_2$).

Anal. Calcd for C$_{16}$H$_{20}$F$_{12}$I$_2$Si$_2$: C, 25.61; H, 2.69; F, 30.39; I, 33.83. Found: C, 25.52; H, 2.60; F, 30.15; I, 33.67.

EXAMPLE II

Preparation of
1,12-Diiodo-1,12-bis(trimethylsilyl)-
3,3,4,4,5,5,6,6,7,7,8,8,9,9,10,10-hexadecafluorododeca-1,11-diene, $(CH_3)_3SiIC\!=\!CH(CF_2)_8CH\!=\!CISi(CH_3)_3$;
1,14-Diiodo-1,14-bis-(trimethylsilyl)-
3,3,4,4,5,5,6,6,7,7,8,8,9,9,10,10,11,11,12,12-eicosafluorotetradeca-1,13-diene,
$(CH_3)_3SiIC\!=\!CH(CF_2)_{10}CH\!=\!CISi(CH_3)_3$; and
1,16-Diido-1,16-bis(trimethylsilyl)-
3,3,4,4,5,5,6,6,7,7,8,8,9,9,10,10,11,11,12,12,13,13,14,14-tetraeicosafluorohexadeca-1,15-diene,
$(CH_3)_3SiIC\!=\!CH(CF_2)_{12}CH\!=\!CISi(CH_3)_3$ This example is similar to EXAMPLE I, except that a mixture of 1,8-diiodoperfluorooctane, 1,10-diiodoperfluorodecane and 1,12-diiodoperfluorododecane was substituted for the 1,6-diiodoperfluorohexane of that example.

Treatment of 16.35 g (0.025 moles) of a mixture of 1,8-diiodoperfluorooctane, 1,10-diiodoperfluorodecane and 1,12-diiodoperfluorododecane with 5 g of trimethylsilylacetylene and 2.5 ml of di-t-butyl peroxide by the procedure of EXAMPLE I after 48 hours of heating gave 16.1 g (95%) of a mixture of the title compounds, an equal mixture of E and Z isomers; proton NMR (CDCl$_3$)δ7.25 (t, 2 H, $J_{HF}$=15 Hz, =CH, E isomer), 6.70 (t, 2 H, $J_{HF}$=13 Hz, =CH, Z isomer), 0.33 (t, 18 H, SiCH$_3$, E isomer) and 0.27 ppm (s, 18 H, SiCH$_3$, Z isomer); fluorine NMR (CDCl$_3$) φ 108.4 (m, 4 F, CH—CF$_2$, E isomer) 111.6 (m, 4 F, CHCF$_2$, Z isomer) 123.2 (m, CF$_2$ internal) and 124.2 ppm (m, =CH—CF$_2$—CF$_2$).

EXAMPLE III

This is an example of the addition reaction of EXAMPLES I and II but utilizing monofunctional iodide in place of the diiodide (or diiodides) in those examples. The product is 1-Iodo-1-trimethylsilyl-3,3,4,4,5,5,6,6,7,7,8,8,9,9,-pentadecafluoro-1-nonene, and is convertible to a monofunctional acetylene when subjected to the dehydrohalogenation and silyl group removal steps of Reaction Scheme I.

A mixture of 3.0 g (6.0 mmol) of perfluoroheptyl iodide, 0.60 g (6.0 mmol) of trimethylsilylacetylene and 0.5 ml of di-t-butyl peroxide was sealed in a glass tube under nitrogen and heated at 120° C. for 48 hrs. The product was dissolved in methylene chloride dried over magnesium sulfate, and stripped of solvent under vacuum to give 3.31 g (92%) of a colorless oil, an equal mixture of E and Z isomers of the title compound. The isomers were separated by GC: E isomer proton NMR (CDCl$_3$): δ7.10 (t, 1 H, $J_{HF}$=15 Hz, =CH) and 0.33 ppm (t, 9 H, SiCH$_3$); fluorine NMR (CDCl$_3$) φ 85.2 (t, 3 F, CF$_3$), 108.4 (q, 2 F, =CH—CF$_2$), 124 (m, 8 F, CF$_2$) and 127.6 ppm (m, 2 F, =CHCF$_2$CF$_2$); Z isomer proton NMR (CDCl$_3$)δ6.58 (t, $J_{HF}$=12 Hz, 1 H, =CH) and 0.25 ppm (S, 9 H, SiCH$_3$); fluorine NMR (CDCl$_3$) φ 85.2 (t, 3 F, CF$_3$), 111.8 (q, 2 F, =CHCF$_2$), 124 (m, 8 F, CF$_2$) and 127.6 ppm (m, 2 F, —CHCF$_2$CF$_2$).

Anal. Calcd for C$_{12}$H$_{13}$F$_{15}$ISi: C, 24.14; H, 2.19; F, 47.72; I, 21.25. Found: C, 23.93; H, 1.99; F, 47.60; I, 21.57.

EXAMPLE IV

This is an example of the preparation of a diacetylene in accordance with this invention from the product of EXAMPLE I, by subjecting the latter to the dehydrohalogenation and silyl removal steps of Reaction Scheme I. The resulting diacetylene was 3,3,4,4,5,5,6,6,7,7,8,8-dodecafluoro-1,9-decadiyne, HC≡C(CF$_2$)$_6$C≡CH.

A mixture of 15 g of potassium t-butoxide and 250 ml of methylene chloride was stirred under nitrogen at −20° C. and 12.8 g (0.017 mole) of 1,10-diiodo-1,10-bis(trimethylsilyl)-3,3,4,4,5,5,6,6,7,7,8,8-dodecafluorodeca-1,9-diene was added dropwise. The slurry was stirred for 1 hour at −20° and for 4 hours at 0°, and then 100 ml of 3N hydrochloric acid was added to neutralize excess potassium t-butoxide. The mixture was stirred for 1 hour, and the organic layer was washed with water, dried and distilled to give 1.92 g (32.5%) of the title compound, bp 55°–59° (15–20 mm): proton NMR (CDCl$_3$)δ2.93 ppm (t, 2 H, J$_{HF}$=4.5 Hz, CH); fluorine NMR (CDCl$_3$) φ 102 (m, 4 F, α−CF$_2$), 123.0 (m, 4 F, γ−CF$_2$) and 124.4 ppm (m, 4 F, β−CF$_2$); IR 3350 (CH), 2200 (C≡C) and 1165 cm$^{-1}$(CF$_2$).

Anal. Calcd for C$_{10}$H$_2$F$_{12}$: C, 34.31; H, 0.57. Found: C, 34.08; H, 0.56.

EXAMPLE V

Preparation of 3,3,4,4,5,5,6,6,7,7,8,8,9,9,10,10-Hexadecafluorododeca-1,11-diyne, HC≡C(CF$_2$)$_8$C≡CH; 3,3,4,4,5,5,6,6,7,7,8,8,9,9,10,10,11,11,12,12-Eicosafluorotetradeca-1,13-diyne, HC≡C(CF$_2$)$_{10}$C≡CH; and 3,3,4,4,5,5,6,6,7,7,8,8,9,9,10,10,11,11,12,12,13,13,14,14-Tetraeicosafluorohexadeca-1,15-diyne, HC≡C(CF$_2$)$_{12}$C≡CH This is an example of the preparation of diacetylenes from a mixture of the products of EXAMPLE II by subjecting them to dehydrohalogenation and silyl group removal procedures in accordance with Reaction Scheme I.

A slurry of 3 g (26 mmol) of potassium t-butoxide in 40 ml of methylene chloride was stirred under nitrogen at −20° C. while 8.2 g of a solution of (CH$_3$)$_3$—SiIC≡CH(CF$_2$)$_8$CH≡CISi(CH$_3$)$_3$, (CH$_3$)$_3$SiIC≡CH(CF$_2$)$_{10}$—CH≡CISi(CH$_3$)$_3$, and (CH$_3$)$_3$SiIC≡CH(CF$_2$)$_{12}$CH≡CISi(CH$_3$)$_3$ in 20 ml of methylene chloride was added dropwise. The reaction mixture was stirred for 1 hour at −20° C. and for 3 hours at 0° C. Potassium fluoride (1.5 g) and 25 ml of t-butanol were then added and the mixture was stirred for 3 hours at ambient temperature. Methylene chloride (100 ml) was added and the solution was washed with five 100 ml portions of water, dried over magnesium sulfate and stripped of solvent. The residue was analyzed by GC using authentic trapped components for calibration, and was shown to contain 1.3 g of HC≡C(CF$_2$)$_8$C≡CH, 0.73 g of HC≡C(CF$_2$)$_{10}$C≡CH and 0.22 g of HC≡C(CF$_2$)$_{12}$C≡CH, for a total yield of 50%. Analytical samples were isolated by GC.

Hexadecafluorododeca-1,11-diyne, HC≡C(CF$_2$)$_8$C≡CH was a colorless liquid: proton NMR (CDCl$_3$)δ2.94 ppm (t, J$_{HF}$=4.5 Hz, CH); fluorine NMR (CDCl$_3$) φ 102 (m, 4 F, α−CF$_2$), 122.8 (m, 8 F, internal fluorine) and 124 ppm (m, 4 F, β−CF$_2$); IR 3355 (CH), 2195 (C≡C) and 1190 cm$^{-1}$(CF$_2$).

Anal. Calcd for C$_{12}$H$_2$F$_{16}$: C, 32.02; H, 0.45. Found: C, 32.44, H, 0.55.

Eicosafluorotetradeca-1,13-diyne, HC≡C(CF$_2$)$_{10}$C≡CH, was a colorless oil: proton NMR (CDCl$_3$)δ2.94 ppm (t, J$_{HF}$=4.5 Hz, CH); fluorine NMR (CDCl$_3$) φ 102 (m, 4 F, α−CF$_2$), 122.8 (m, 12 F, internal F) and 124.2 ppm (m, 4 F, β−CF$_2$); IR 3355 (CH), 2200 (C≡C) and 1195 cm$^{-1}$(CF$_2$).

Anal. Calcd for C$_{14}$H$_2$F$_{20}$: C, 30.57; H, 0.37; F, 69.07. Found: C, 30.27; H, 0.38; F, 68.84.

Tetraeicosafluorohexadeca-1,15-diyne, HC≡C(CF$_2$)$_{12}$C≡CH, was a white solid mp 54°-56°; proton NMR (CDCl$_3$)δ2.94 ppm (t, J$_{HF}$=4.5 Hz, CH); fluorine NMR (CDCl$_3$) φ 102 (m, 4 F, α−CF$_2$), 122.8 (m, 16 F, internal F) and 124.2 ppm (m, 4 F, β−CF$_2$); IR 3355 (CH), 2200 (C≡C) and 1190 cm$^{-1}$ (CF$_2$).

Anal. Calcd for C$_{16}$H$_2$F$_{24}$: C, 29.56; H, 0.31; F, 70.13. Found: C, 29.30; H, 0.31; F, 70.23.

EXAMPLE VI

This is an example of the preparation of the diacetylene 3,3,4,4,5,5,6,6,7,7,8,8-dodecafluoro-1,9-decadiyne, in accordance with Reaction Scheme II.

A mixture of 5.5 g (0.010 mol) of 1,6-diiodoperfluorohexane, 3.4 g (0.020 mol) of bis trimethylsilylacetylene and 0.5 g benzyltriethylammonium chloride was heated in a sealed tube at 140° C. for 85 hours. The mixture was extracted with 100 ml of methylene chloride and the resulting solution was washed with 50 ml of 0.1N sodium thiosulfate and with water, dried over magnesium sulfate and distilled at 75°–100° C. (0.2 mm) to give 1.2 g of a mixture of I(CF$_2$)$_6$C≡CSi(CH$_3$)$_3$ and (CH$_3$)$_3$SiC≡C—(CF$_2$)$_6$C≡CSi(CH$_3$)$_3$. A sample of the latter was isolated by GC: proton NMR (CDCl$_3$)δ0.27 ppm (s); fluorine NMR φ 100.8 (m, 4 F, C≡CCF$_2$), 122.4 (m, 4 F, C≡CCF$_2$CF$_{2CF2}$) and 124 ppm (m, 4 F, C≡CCF$_2$CF$_2$); IR 3020 (CH$_3$), 2245 (C≡C) and 1220 cm$^{-1}$ (CF$_2$).

The above mixture was added to 40 ml of methanol and 2 g of potassium fluoride and the mixture was stirred for 20 hours. Methylene chloride (120 ml) was added and the solution was washed with two 100 ml portions of water dried and stripped of solvent. Preparative GC of the residue gave 0.24 g of 3,3,4,4,5,5,6,6,7,7,8,8-dodecafluoro-1,9-decadiyne, identical with the material described in EXAMPLE IV.

EXAMPLE VII

This is an example of the polymerization of diacetylenes in accordance with this invention.

A 0.2 g sample of a mixture of HC≡C(CF$_2$)$_6$≡CH, HC≡C(CF$_2$)$_8$C≡CH, and HC≡C(CF$_2$)$_{10}$C≡CH was placed in a glass tube, flushed with nitrogen and sealed under vacuum. The tube was heated at 250° for 48 hours, cooled and opened. A clear hard resin was obtained. The resin was stable in air at 350° C.

EXAMPLE VIII

This is an example of the trimerization of a perfluoroalkyl primary acetylene prepared as taught herein. In the example, we employed 3,3,4,4,5,5,6,6,7,7,8,8,9,9,9-pentadecafluorononyne-1, CF$_3$—(CF$_2$)$_6$C≡CH as the starting material. The product was found to be a mixture of 1,3,5-tris(perflurohheptyl)benzene and 1,2,4-tris(perfluoroheptyl)benzene in a ratio of 1:10 to 1:6. The mixture was liquid, although the pure 1,3,5 isomer is a solid, mp 45° C. Materials of this type have characteristics which render them suitable as thermally stable lubricating oils, hydraulic fluids, etc. Mixtures of acetylenes with different chain lengths can be used to lower the melting points, and copolymers with small amounts of fluorinated diacetylenes can be used to reduce the volatility.

A sealed glass tube containing 0.373 g (0.95 mmole) of 3,3,4,4,5,5,6,6,7,7,8,8,9,9,9-pentadecafluorononyne-1 under nitrogen was heated at 255° C. for 65 hours. The resulting viscous liquid (0.352 g) was shown by NMR and GC to be a 10:1 mixture of 1,3,5-tris(perfluoroheptyl)benzene and 1,2,4-tris(perfluoroheptyl)benzene. Pure samples of the compounds were isolated by GC. The 1,3,5 isomer was a white solid mp 45.0°–45.5° C.: $^1$H NMR (CFCl$_3$)$\delta$8.08 (s); $^{19}$F NMR (CFCl$_3$) $\phi$ 85.6 (t, J=10 Hz, 9 F, CF$_3$), 114.4 (t, J=15 Hz, 6 F, ArCF$_2$), 124.0 (m, 24 F) and 128.2 (broad s, 6 F).

Anal. Calcd for C$_{33}$H$_3$F$_{45}$: C, 27.43; H, 0.26. Found: C, 26.62; H, 0.26.

The 1,2,4 isomer was a colorless liquid: $^1$H NMR (CDCl$_3$)$\delta$7.83 (s, 1 H), 7.88 (d, J=6 Hz, 2 H); $^{19}$F NMR (CFCl$_3$) $\phi$ 85.6 (t, J=10 Hz, 9 F, CF$_3$), 106.6 (m, 2 F, ArCF$_2$), 114.6 (m, 2 F), 120.3 (m, 2F), 123.9 (m, 24 F) and 128.2 (m, 6 F).

Anal. Calcd for C$_{33}$H$_3$F$_{45}$: C, 27.43; H, 0.26. Found: C, 28.21; H, 0.32.

To clear up what might appear to be an inconsistency between Reaction Scheme I as set forth in its general form above and specific applications of its iodide elimination step in the foregoing examples, it should be pointed out that a choice of more than one base is suitable for use in that step. Of these, the preferred ones are DBU and potassium t-butoxide, the former, we have now discovered, being superior to the latter. More specifically, it has been found that the use of DBU in lieu of potassium t-butoxide in said iodide elimination step can result in a product yield of 60%, as compared to the 32.5% yield of EXAMPLE IV. Likewise, the silyl radicals can be removed from our trimethyl silylacetylene compounds through the use of fluoride ions (KF being a preferred fluoride agent for the purpose) or a base such as potassium t-butoxide or DBU.

It is preferable, but not critically necessary, to remove all of the iodide from the addition product of the diiodide and trimethylsilylacetylene in Reaction Scheme I before the silyl is removed. Any reaction condition or conditions adequate to break the iodide bond can be employed for that purpose. We have found temperature control satisfactory in this regard, lower temperatures being better than higher ones. For example, as EXAMPLES IV and V illustrate, we found that a temperature of −20° C. achieved good results in the elimination of the iodide. This was found to be true when using either DBU or potassium t-butoxide as the base in that step of the procedure. Complete replacement of all of the iodide radicals by acetylene bonds is, as previously indicated, desirable (although not critically necessary) so that there will be no excess diiodide in the final reaction mixture. This means that the initial, addition step of Reaction Scheme I should preferably be continued long enough for complete reaction of the diiodide. If less than complete reaction takes place, there will be difficult separation problems in the final mixture. Consequently, a large excess of the silylacetylene reactant should, for best results, be employed in the addition step of the method.

Our silylacetylene reactants are available commercially. The diiodide reactants, on the other hand, are not commercially available, but a method of preparing them has been reported by two of us (Kurt Baum and Clifford D. Bedford) under the title "Preparation of α,ω-Diiodoperfluoroalkanes" in the Journal of Organic Chemistry, 45, 347(1980).

Subsequent to our completion of the work reported in EXAMPLES I through VII, above, we discovered a variation of Reaction Scheme II in which the first step of that procedure (reaction of fluorocarbon iodides with bis(trimethylsilyl)acetylene to obtain trimethylsilylacetylenes directly) can be achieved under the influence of heat, rather than quaternary ammonium salts or dimethylformamide. EXAMPLE IX, below, is illustrative of this development.

EXAMPLE IX

Preparation of 1,10-bis(trimethylsilyl)perfluorodeca-1,9-diyne, (CH$_3$)$_3$SiC≡C(CF$_2$)$_6$C≡CSi(CH$_3$)$_3$ A glass tube containing 2.00 g (3.60 mmole) of 1,6 diiodoperfluorohexane, 1.24 g (7.30 mmole) of bis(trimethylsilyl)acetylene and 0.12 g (0.47 mmole) of iodine was sealed under vacuum and heated for 24 hours at 200° C. Distillation of the mixture gave 1.09 g of liquid, bp 70°–84° C. (0.02–0.03 mm) which was shown by GC analysis to contain 60% of 1,10-bis(trimethylsilyl)perfluorodeca-1,9-diyne (37% yield). A sample of the pure compound was isolated by preparative GC; its spectra were identical with those reported in EXAMPLE VI.

Further work, following that reported in EXAMPLE IX, resulted in the successful preparation of trimethylsilylacetylenes by a procedure like that of EXAMPLE IX, except without the addition of any free iodine. This achievement was made possible by the presence of liberated iodine from the fluorocarbon iodide reactants in the reaction zone.

We have heretofore only considered high-temperature methods of polymerizing the perfluoroalkylene compounds of this invention in which the compounds are subjected to relatively high temperatures over relatively long periods of time (the temperature in Example VII, for instance, being 25° C., and the heating time, 48 hours). Such high temperatures and prolonged heating times can, however, be very significantly reduced through the use of suitable catalysts. This is convincingly demonstrated by the following example illustrating the use of such a catalyst.

EXAMPLE X 0.64 Grams of HC≡C(CF$_2$)$_8$C≡CH was mixed with 0.16% by weight of bis(benzonitrile)palladium (II) chloride, (C$_6$H$_2$)$_2$PdCl$_2$. The mixture was heated for thirty minutes at 90° C. This resulted in the formation of a clear glassy polymer similar to that obtained by prolonged heating at a high temperature in the absence of a catalyst (for example, the resin obtained in Example VII). The (C$_6$H$_5$)$_2$PdCl$_2$ served as a catalyst in this example to effectuate a greatly reduced temperature and heating time by comparison, for example, with the temperature and heating time of Example VII.

Other polymers similar to the product of EXAMPLE X were obtained from HC≡C(CF$_2$)$_8$C≡CH through the use of the below-listed catalysts in procedures similar to that of EXAMPLE X, but employing the following catalyst quantities, temperatures and heating times.

| Catalyst | % by Weight of Catalyst | Heating Temperature (°C.) | Heating Time (Hours) |
|---|---|---|---|
| Molybdenum hexacarbonyl | 1 | 160 | 2 |
| Nickel (II) acetylacetonate | 0.72 | 160 | 8 |
| bis(Triphenylphosphene)-nickel (II) bromide | 0.6 | 160 | 16 |
| bis(Triphenylphosphene)-nickel (II) cyanide | 1 | 160 | 16 |

There are, of course, cost saving advantages in the substantially lower temperatures and shorter heating times made possible by the use of catalysts in the polymerization reactions of this invention. Of significance in this connection, moreover, is the fact that such lower temperatures permit the polymerizations to be conducted below the boiling points of the perfluoroalkylene acetylenes without pressure equipment.

Variant forms of the term "trimerize" have been herein loosely employed to denote not only trimerization in the strict sense of the term (such as, for example, occurs in the trimerization of monofunctional acetylene compounds where there is no cross-linking between the trimers thus formed) but also the formation of such trimers and polymerization thereof to form cross-linked products (such as occurs when the diacetylene compounds of our invention are polymerized). Although this rather loose usage of the terms in question is common among chemists and does not, we feel, lead to confusion in their minds as to what the terms are intended to mean, in order to avoid indefiniteness in the language of our claims, those claims have been carefully drafted to employ "trimerization," or a variant form of that term, only when the polymerization of monoacetylene compounds is involved where there can be no cross-linking of the resultant trimers.

As will now be apparent, the reach of the present invention is widespread to cover numerous aspects and modifications of its common theme. The following claims are structured to encompass this diverse subject matter and it should be noted that the scope of the invention extends to all variant forms thereof within the ambit of the claim language.

We claim:

1. As a composition of matter, a perfluoroalkylene $\alpha,\omega$-diacetylene having the formula $HC\equiv C(CF_2)_nC\equiv CH$, wherein n is a whole number from 5 to about 20, inclusive.

2. A composition of matter in accordance with claim 1 in which n is 6, 8, 10 or 12.

* * * * *

UNITED STATES PATENT AND TRADEMARK OFFICE
CERTIFICATE OF CORRECTION

PATENT NO. : 4,618,734
DATED : October 21, 1986
INVENTOR(S) : Kurt Baum, Ronald O. Hunadi and Clifford D. Bedford It is certified that error appears in the above-identified patent and that said Letters Patent are hereby corrected as shown below:

Column 1, line 32, change the period (.) after "resins" to a comma (,).
Column 3, line 66, cancel "111.6 (m, =CH-$\underline{CF_2}$-, E isomers),". Column 5, line 16, "3N" should be --3 $\underline{N}$--. Column 6, lines 3 and 4, "HC≡C($CF_2$)$_1$oC≡CH" should be --HC≡C($CF_2$)$_{10}$C≡CH--; line 36, "C≡C$CF_2$$CF_2$$CF2$" should be --C≡C$CF_2$$CF_2$$\underline{CF_2}$--; and line 51, "HC≡C($CF_2$)$_6$≡CH" should be --HC≡C($CF_2$)$_6$C≡CH--. Column 8, line 4, "45" should be underlined; line 19, "($CH_3$)$_3$SiC≡C($CF_2$)$_6$≡CSi($CH_3$)$_3$" should be --($CH_3$)$_3$SiC≡C($CF_2$)$_6$C≡CSi($CH_3$)$_3$--; and line 44, "25°" should be --250°--.

Signed and Sealed this

Seventeenth Day of February, 1987

*Attest:*

DONALD J. QUIGG

*Attesting Officer*  *Commissioner of Patents and Trademarks*